United States Patent [19]

Narita et al.

[11] Patent Number: 5,003,076
[45] Date of Patent: Mar. 26, 1991

[54] BENZOTRIAZOLE DERIVATIVES AND CHIRAL DERIVATIZATION REAGENTS FOR CARBOXYLIC ACIDS THEREOF

[75] Inventors: Shigeru Narita; Takayasu Kitagawa, both of Osaka, Japan

[73] Assignee: Shionogi & Co., Ltd., Osaka, Japan

[21] Appl. No.: 412,772

[22] Filed: Sep. 26, 1989

[30] Foreign Application Priority Data

Oct. 12, 1988 [JP] Japan .................................. 63-257943
Jun. 5, 1989 [JP] Japan .................................... 1-142348

[51] Int. Cl.$^5$ ............................................. C07D 249/20
[52] U.S. Cl. ................................... 548/259; 548/257; 548/260; 562/402
[58] Field of Search ......................... 548/260, 259, 257

[56] References Cited

U.S. PATENT DOCUMENTS 4,378,361  3/1983  Schromm ............................ 548/260
4,791,206 12/1988  O'Neil ................................ 548/260

OTHER PUBLICATIONS

Chem. Abst., vol. 111, Entry 146033v (1989).
Chem. Abstr., vol. 111, Entry 208455v (1989).
Chemical Abstracts, vol. 94, Entry 53433r (1981).
Narita et al., Analytical Sciences, vol. 5, pp. 361-362 (Jun. 1989).

Primary Examiner—Donald G. Daus
Attorney, Agent, or Firm—Wenderoth, Lind & Ponack

[57] ABSTRACT

Novel fluorescent chiral derivatization reagent containing a compound of the formula:

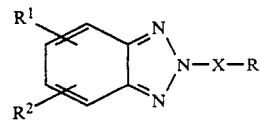

being useful for the determination of carboxylic acid enantiomers with high sensitivity, which are easily and well separated in a form of their consequent diastereomeric amides.

6 Claims, 1 Drawing Sheet

BENZOTRIAZOLE DERIVATIVES AND CHIRAL DERIVATIZATION REAGENTS FOR CARBOXYLIC ACIDS THEREOF

BACKGROUND OF INVENTION

1. Field of the Invention

There exist many optically active substances in pharmaceuticals, but they are often used in a form of (±)-racemates. However, it is known that one enantiomer is sometimes quite different from the other in activity or toxicity or in metabolism and, therefore, it is necessary to evaluate each enantiomer individually. This invention relates to compounds suitable especially for microanalysis of optical isomers of carboxylic acids among optically active compounds, and to fluorescent chiral derivatization reagents containing said compound.

2. Prior Art

As for fluorescent chiral derivatization reagents that are capable of analyzing optically active carboxylic acids with high sensitivity, hitherto there have been only the following three kinds: Goto et al. analyzed N-acetylamino acids and α-allyl propionic acids by normal-phase high performance liquid chromatography (HPLC) with the use of 1-(4-dimethylamino-1-naphthyl)ethylamine (J. Goto et al.: Anal. Chim. Acta, 120, 187 (1980)). In addition, as a reagent 10 times as sensitive as the aforesaid reagent, they disclosed 1-(1- or 2-anthryl)ethylamine (J. Goto et al.: J. Liq. Chromatogr., 9, 683 (1986)).

However, even with 1-(1 or 2-anthryl)ethylamine, the detection limit is 100 fmol, which is still not necessarily sensitive enough. Thus, it has not been used in the reverse-phase HPLC, which is more advantageous than the normal-phase HPLC in analysis of samples taken from living bodies.

SUMMARY OF INVENTION

The subject compounds of the following formula:

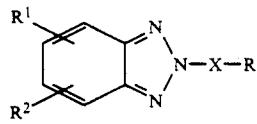

wherein X is phenylene or naphthylene; $R^1$ and $R^2$ are, both identically or differently from each other, hydrogen, $C_1$-$C_5$ alkyl, $C_1$-$C_5$ alkyloxy, amino or mono- or di-$C_1$-$C_5$ alkylamino or jointly form $C_1$-$C_5$ alkylene or $C_1$-$C_5$ alkylenedioxy; and R is a group represented by the formula:

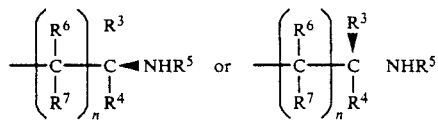

in which $R^3$ and $R^4$ are, differently from each other, hydrogen, $C_1$-$C_5$ alkyl, $C_1$-$C_5$ alkyloxy, cyano, $C_1$-$C_5$ alkyloxycarbonyl, or $C_1$-$C_5$ alkylcarbonyl; $R^5$ is hydrogen or $C_1$-$C_5$ alkyl; $R^6$ and $R^7$ each is identically or differently hydrogen, $C_1$-$C_5$ alkyl, $C_1$-$C_5$ alkyloxy, cyano, $C_1$-$C_5$ alkyloxycarbonyl or $C_1$-$C_5$ alkylcarbonyl; and n is an integer of 0-2 or the salt thereof (hereafter referred to simply as the compounds of this invention) are very useful in measuring optically active carboxylic acids with high sensitivity.

DESCRIPTION OF PREFERRED EMBODIMENTS

Problems to be Solved

Figure 1:
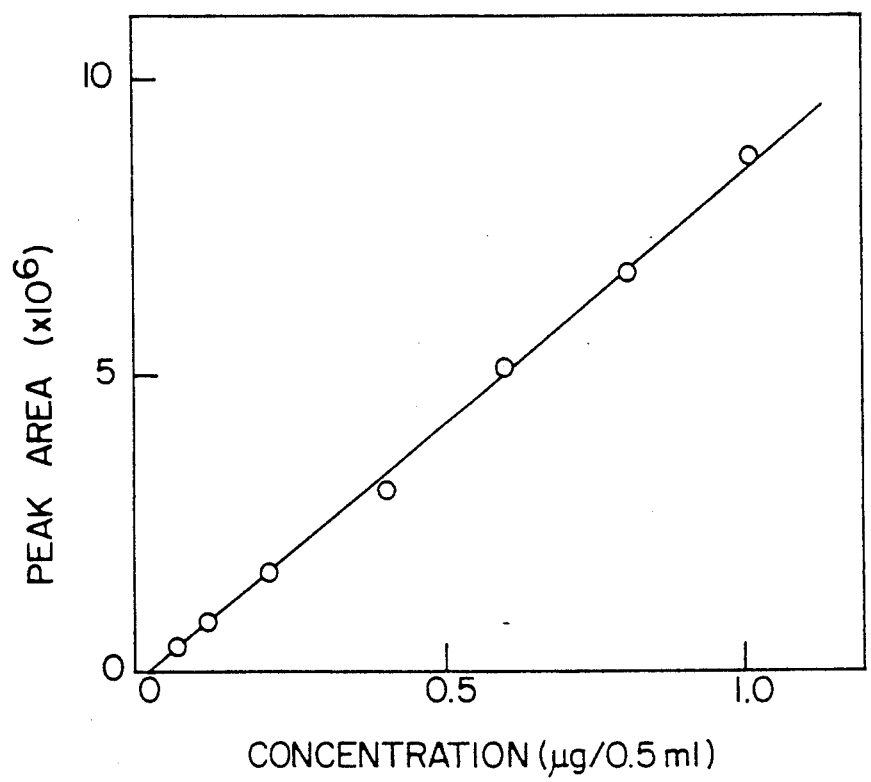
FIG. 1 illustrates the relationship between the concentration of the compound A (described hereinafter) and the peak area of the chromatogram, with the ordinate showing the peak area ($\times 10^6$) and the abscissa the concentration of the compound A ($\mu g/0.5$ ml).

In view of the above circumstances, the inventors tried to develop a fluorescent chiral derivatization reagent which is more sensitive than the conventional reagents, and besides, is capable of effectively separating isomers even in the reverse-phase HPLC. As a result, this invention was completed.

Means to Solve the Problem

The subject compounds of the present invention react with optically active carboxylic acids at room temperature in the presence of a condensing agent. The reaction products are diastereomeric amides having strong fluorescence, and are satisfactorily separated in the reverse-phase HPLC. Moreover, the excess reagent can be removed easily. Thus, the compounds of this invention are those useful in making it possible to easily measure optically active carboxylic acids with high sensitivity.

The compounds of this invention react with optically active carboxylic acids in an aprotic solvent in about 1-2 hours at room temperature in the presence of a condensing agent and a base or an acid-scavenger in place of the base, thereby forming corresponding diastereomeric amides having strong fluorescence. Besides, any excess reagents can be removed easily by passing the reaction solution through a silica column for pretreatment. It is desirable that the substituents $R^1$ and $R^2$ are highly electron donating, since the high electron donative property gives a high fluorescence intensity to the resulting compound.

The compounds of this invention can be obtained easily by known reactions in the field of organic chemistry. For example, as shown below, substituted aniline (a) is subjected to conventional reaction, by a known diazo coupling reaction (Step 1), with diazo compound (b) having an optically active aminoalkyl group protected by a suitable protecting group, then to oxidative ring-closing reaction (Step 2), followed by deprotection (Step 3), to give the compounds of this invention.

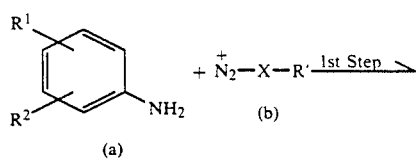

3

-continued

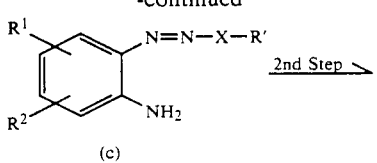

(c)

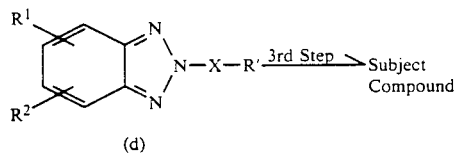

In the reaction scheme illustrated above, $R^1$, $R^2$ and $X$, each has the same meaning as defined above and $R'$ represents a group of the formula:

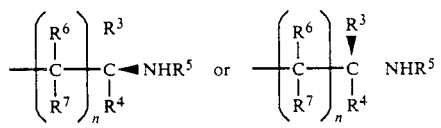

Reactions are explained hereunder step by step.

Step 1

The reaction in this step is usually carried out in an aqueous solution at a temperature from ice-cooled to 15° C. An optically active aniline or naphthylamine derivative corresponding to the diazo compound (b) is dissolved or suspended in an inorganic acid, which is then reacted with a nitrous acid such as sodium nitrite to obtain the highly reactive diazo compound (b). To remove excess nitrous acid, sulfamic acid or urea is added to decompose the excess nitrous acid.

Next, the substituted aniline compound (a) is added thereto, which is easily coupled with the diazo compound (b) to give the compound (c). The reaction is completed in several minutes to several hours.

Step 2

The azo group of the compound (c) easily undergoes an oxidative ring closure with the adjacent amine group to give the triazole compound (d). The reaction is completed in several minutes to several ten hours at room temperature or under heating, if carried out in a water-containing organic solvent in the presence of a copper-ammonia complex.

Step 3

This step gives the compounds of this invention by de-protection. The compound (d) is subjected to hydrolysis in a water-containing organic solvent in the presence of an acid to give the compounds of this invention. The reaction is completed in several minutes to several days at room temperature or under heating.

In this invention, $C_1$–$C_5$ alkylene means a straight chain $C_1$–$C_5$ alkylene, including methylene, ethylene, propylene, butylene, and pentylene. Especially, methylene or ethylene is preferable.

$C_1$–$C_5$ alkyl means straight or branched chain $C_1$–$C_5$ alkyl, including methyl, ethyl, p-propyl, isopropyl, n-butyl, sec-butyl, tert-butyl, n-pentyl, isopentyl, neopentyl, tert-pentyl, etc.

As for the protecting group, all the known protecting groups for an amine group can be used. Among others, those stable in acids are preferable, for example, acetyl, trifluoroacetyl, benzoyl and the like.

4

The salt can be an acid addition salt.

The present invention is further explained in the following Examples and Experiment Examples, which are not intended to limit the scope of this invention.

EXAMPLE

Example 1

Preparation of
S-(−)-2-[4-(1-aminoethyl)naphthyl]-6-methoxy-N-methyl-2H-benzotriazolyl-5-amine.dihydrochloride (1)

To a solution of (1S)-1-(4-aminonaphthyl)-N-acetylethylamine (2.3 g) in 50 ml of 10% hydrochloric acid was added 7% sodium nitrite (10 ml), while being stirred under ice-cooling. 15 minutes later, 10% aqueous solution of ammonium sulfamate (10 ml) was added thereto, and the mixture was stirred for 15 minutes. The reaction mixture was adjusted to about pH 5 with sodium acetate, then combined with 4-amino-2-N-methylaminoanisole.dihydrochloride (2.3 g) and the resulting mixture was stirred further for 4 hours. The reaction mixture was then adjusted to about pH 9 with 1N aqueous solution of sodium hydroxide and extracted with ethyl acetate. The ethyl acetate was distilled off, and the residue was dissolved in a small quantity of ethanol, which was then added to a 1M hydrochloric acid-ethyl ether solution (50 ml), whereby the azo compound was obtained as dark red powders (3.5 g).

To a solution of the azo compound (3.4 g) dissolved in pyridine (50 ml) was added an ammoniacal cupric sulfate solution (which were prepared by dissolving 10 g of cupric sulfate pentahydrate and 10 g of ammonium chloride in 50 ml of water and neutralizing the solution with sodium hydrogencarbonate), and the mixture was refluxed for 1 hour. After completion of the reaction, the solution was cooled and then extracted with ethyl acetate. The ethyl acetate was evaporated, and the residue was dissolved in ethanol (50 ml). To this was added 30 ml of 10% hydrochloric acid, and the mixture was refluxed for 5 days.

After completion of the reaction, the reaction mixture was evaporated to give a residue, which was dissolved in a small quantity of ethanol, then added to a 1M hydrochloric acid-ethyl ether solution. The precipitate was collected by filtration, which was then recrystallized from ethyl ether-methanol, whereby the objective compound (1) was obtained as light yellow needles, m.p. 225°–257° C.

IR (Nujol): 1610, 1640, 3400 cm$^{-1}$.

$[\alpha]_D^{23}$ −16.8° (c=1, methanol).

Elemental Analysis for $C_{20}H_{23}N_5OCl_2 \cdot H_2O$: Calcd: C, 54.80; H, 5.75; N, 15.98; Cl, 16.18, Found: C, 54.92; H, 6.06; N, 16.07; Cl, 15.97.

Example 2

Preparation of
S-(−)-2-[p-(1-aminoethyl)phenyl]-N,N-dimethyl-2H-benzotriazolyl-5-amine.dihydrochloride (2)

The reaction was performed in the same manner as in Example 1 except that S-1-(4-aminophenyl)-N-acetylethylamine in place of (1S)-1-(4-aminonaphthyl)-N-acetylethylamine and N,N-dimethyl-m-phenylenediamine.dihydrochloride in place of 4-amino-2-N-methylaminoanisole.dihydrochloride were used.

Moreover, the precipitated azo compound was collected by filtration and recrystalized from isopropanol. Recrystallization of the objective compound (2) was done alone from methanolisopropanol, colorless needles, m.p. 257°-260° C. (decomp).

IR (Nujol): 1650, 2460 cm$^{-1}$.

$[\alpha]_D^{26}$: −7.5° (c=1.07, methanol).

Elementary Analysis for $C_{16}H_{21}N_5Cl_2$: Calcd: C, 54.24; H, 5.97; N, 19.77; Cl, 20.01, Found: C, 54.09; H, 5.98; N, 19.56; Cl, 20.02.

Experiment Examples

General Procedures for Analysis 0.5 ml of acetonitrile solution containing an optically active carboxylic acid is placed into a 10-ml vial. To this are added 50 μl each of acetonitrile solutions of 2-bromo-1-ethyl-pyridinium tetrafluoroborate (3.7 mM), 9-methyl-3,4-dihydro-2H-pyrido[1,2-a]pyrimidin-2-one (2.7 mM) and the compound of this invention (3.7 mM), which is then agitated for about 10 seconds. The mixture is allowed to stand at room temperature for about 2 hours. 0.5 ml of this reaction solution is passed through a pretreatment silica column, and eluted with acetonitrile (1.5 ml). The whole quantity of the eluate is made 2.5 ml with acetonitrile, of which 20 μl is subjected to HPLC.

Experiment Example 1

The Compound (1) of this Invention is used as a Reagent

Acetonitrile solutions (0.5 ml each) containing 0.05, 0.1, 0.2, 0.4, 0.6, 0.8 or 1 μg each of 5-(N,N-dimethylsulfamoyl)-6,7-dichloro-2,3-dihydrobenzofuran-2-carboxylic acid (hereafter referred to as compound A) were taken into 10-ml vials. To each of these vials are added acetonitrile solutions (50 μl each) of 2-bromo-1-ethylpyridinium tetrafluoroborate (3.7 mM), 9-methyl-3,4-dihydro-2H-pyrido[1,2-a]pyrimidin-2-one (2.7 mM) and the compound (1) of this invention (3.7 mM), which was then agitated for 10 seconds, and the mixture was allowed to stand at room temperature for about 2 hours. 0.5 ml of each of these reaction solutions was passed through Bond Elut ® (silica), and eluted with acetonitrile (1.5 ml). The whole quantity of the eluate was made 2.5 ml with acetonitrile, of which 20 μl was subjected to HPLC.

Conditions for Measurement

Apparatus: Shimadzu LC-4A Pump (Shimadzu) Shimadzu RF-535 Fluorescence HPLC Monitor.
Column: Nucleosil 5C$_{18}$ (4.6×250 mm; Nagel).
Guard Column: Nucleosil 5C$_{18}$ (4.6×250 mm; Nagel).
Mobile Phase: Acetonitrile-water (3:2 mixture by v/v).
Flow Rate: 1.0 ml/min.
Wavelength: 355 nm for excitation, 480 nm for emission.

Results

Figure 2:
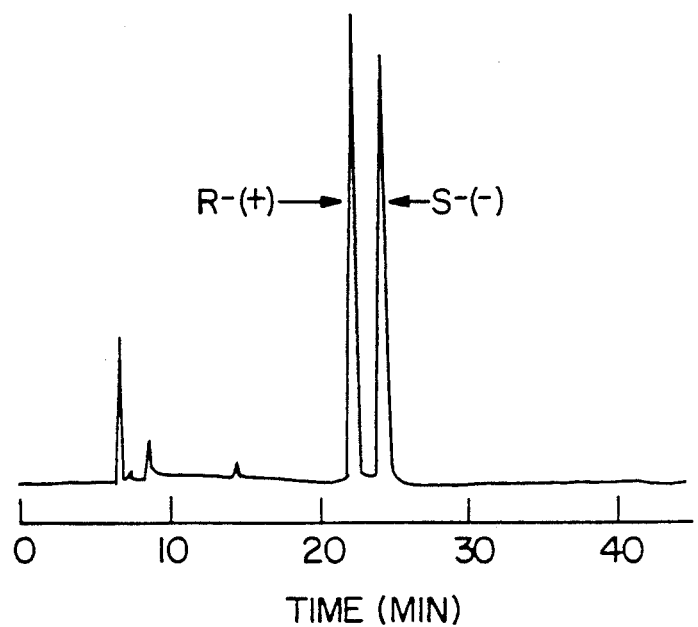
FIG. 2 is the chromatogram obtained in Experiment Example 1. The ordinate shows retention time (minute). The peaks shown by the arrows are R-(+) form and S-(−) form (about 2 ng) of the compound A.

The relationship between the concentration of the compound A and the peak area of the chromatogram obtained in the Experiment above is shown in FIG. 1 and the chromatogram is shown in FIG. 2.

Experiment Example 2

The Compound of this Invention (1) is used as a Reagent

On the acetonitrile solutions (0.5 ml each) each containing 1 μg of Ibuprofen, 2-phenylproionic acid or 2-phenyl-n-butylic acid, the same procedure as in Experiment Example 1 was carried out, using the compound (1) of this invention as a reagent.

Conditions for Measurement

The same conditions were followed on the apparatus, column, guard column, flow rate, and wavelength for measurement as Experiment Example 1.
Mobile Phase:
Acetonitrile/water =
2/1 (Ibuprofen),
4/3 (2-phenylpropionic acid, 2-phenyl-n-butylic acid)

Results

The data on optical resolution of each compound are shown in Table 1, together with the data on compound A.

TABLE 1

|  | k' | α | Rs |
| --- | --- | --- | --- |
| Compound A | (+) 7.32 (−) 8.13 | 1.11 | 2.12 |
| Ibuprofen | (+) 8.29 (−) 9.27 | 1.12 | 2.18 |
| 2-Phenyl Propionate | (+) 6.39 (−) 7.02 | 1.10 | 1.78 |
| 2-Phenyl n-butylate | (+) 8.95 (−) 9.57 | 1.07 | 1.29 |

In Table 1 above, k', α and Rs refer to capacity ratio, separation factor and resolution value, respectively.

Experiment Example 3

The Compound of this Invention (2) is used as a Reagent

Solutions of 1 μg each of compound A, Naproxen and Ibuprofen, each in 0.5 ml of acetonitrile, were prepared. For each of these solutions, the procedure of Experiment Example 1 was followed except that the compound (2) of this invention was used as a reagent.

Conditions of measurement

The same measuring apparatus, column, guard column and flow rate as in Experiment Example 1 were used.
Wavelength: 395 nm for excitation, 510 nm for emission.
Mobile Phase: Acetonitrile/water =
3/2 (Compound A),
5/3 (Naproxen),
2/1 (Ibuprofen).

Results

The data on the separation of isomers of each compound which were obtained from the above experiment are shown in Table 2.

TABLE 2

|  | k' | α | Rs |
| --- | --- | --- | --- |
| Compound A | (+) 7.44, (−) 8.10 | 1.09 | 1.70 |
| Naproxen | (+) 6.69, (−) 7.62 | 1.14 | 3.24 |
| Ibuprofen | (+) 9.93, (−) 10.73 | 1.08 | 1.84 |

In Table 2 above, k', α and Rs refer to capacity ratio, separation factor and resolution value, respectively.

In the above experiment examples, tests were made of specific compounds of this invention. However, it should be noted that this invention is not limited to these compounds. Exemplified below are representative examples of desirable compounds of this invention:

(1) R-(+)-2-[4-(1-aminoethyl)naphthyl]-6-methoxy-N-methyl-2H-benzotriazolyl-5-amine.dihydrochloride, (2) S- or R-2-[p-(1-aminoethyl)phenyl]-N,N-dimethyl-2H-benzotriazolyl-5-amine.dihydrochloride, (3) S- or R-3-[p-(5,6-methylenedioxy-2H-benzotriazol-2-yl)]-2-propylamine, and (4) S- or R-1-[p-(5,6-dimethoxy-2H-benzotriazol-2-yl)]-1-propylamine.

What is claimed is:

1. A compound represented by the formula:

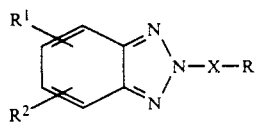

wherein X is phenylene or naphthylene; $R^1$ and $R^2$ each is, identically or differently from each other, hydrogen, $C_1$-$C_5$ alkyl, $C_1$-$C_5$ alkyloxy, amino or mono- or di-$C_1$-$C_5$ alkylamino, or jointly may form $C_2$-$C_5$ alkylene attached to adjacent carbons or $C_1$-$C_5$ alkylenedioxy attached to adjacent carbons; and R is a group represented by the formula:

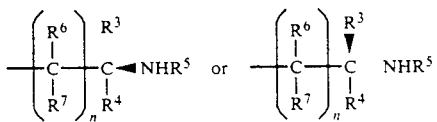

in which $R^3$ and $R^4$ are, differently from each other, hydrogen, straight chain $C_1$-$C_5$ alkyl, $C_1$-$C_5$ alkyloxy, $C_1$-$C_5$ alkyloxycarbonyl, or $C_1$-$C_5$ alkylcarbonyl; $R^5$ is hydrogen or $C_1$-$C_5$ alkyl; $R^6$ and $R^7$ each is, identically of differently from each other, hydrogen, straight chain $C_1$-$C_5$ alkyl, $C_1$-$C_5$ alkyloxy, $C_1$-$C_5$ alkyloxycarbonyl, or $C_1$-$C_5$ alkylcarbonyl; and n is selected from 0, 1, or 2; or an acid addition salt thereof.

2. The compound claimed in claim 1, namely, (S)-2-[4-(1-aminoethyl)-naphthyl]-6-methoxy-N-methyl-2H-benzotriazolyl-5-amine dihydrochloride.

3. The compound claimed in claim 1, namely, (R)-2-[4-(1-aminoethyl)-naphthyl]-6-methoxy-N-methyl-2H-benzotriazolyl-5-amine dihydrochloride.

4. The compound claimed in claim 1, namely, (S)-2-[p-(1-aminoethyl)-phenyl]-N,N-dimethyl-2H-benzotriazolyl-5-amine dihydrochloride.

5. The compound claimed in claim 1, namely, (R)-2-[p-(1-aminoethyl)-phenyl]-N,N-dimethyl-2H-benzotriazolyl-5-amine dihydrochloride.

6. A chiral derivatization reagent for optically active carboxylic acids, containing the compound claimed in any one of claims 2 to 5 and 1, a condensing agent, and a base or an acid-scavenger in an aprotic solvent.

* * * * *

UNITED STATES PATENT AND TRADEMARK OFFICE
CERTIFICATE OF CORRECTION

PATENT NO. : 5,003,076
DATED : March 26, 1991
INVENTOR(S) : Shigeru Narita, et al.

It is certified that error appears in the above-identified patent and that said Letters Patent is hereby corrected as shown below:

Column 1, lines 55-60, rewrite as

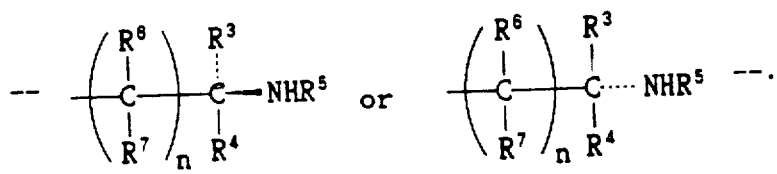

Column 3, lines 20-25, rewrite as

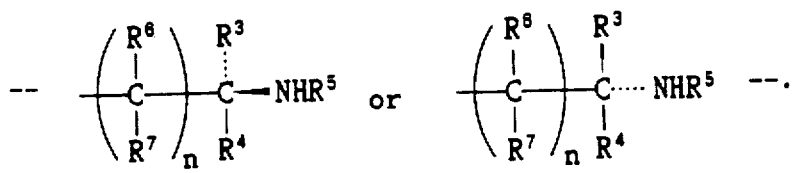

UNITED STATES PATENT AND TRADEMARK OFFICE
CERTIFICATE OF CORRECTION

PATENT NO. : 5,003,076

DATED : March 26, 1991

INVENTOR(S) : Shigeru Narita, et al.

It is certified that error appears in the above-identified patent and that said Letters Patent is hereby corrected as shown below:

Column 8, lines 1-7, rewrite as

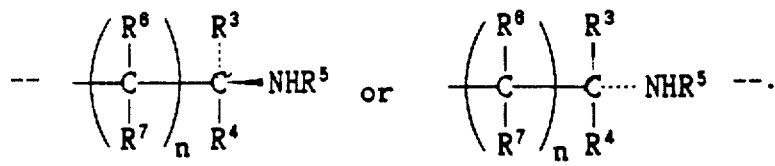

Signed and Sealed this

Third Day of November, 1992

Attest:

DOUGLAS B. COMER

Attesting Officer

Acting Commissioner of Patents and Trademarks